United States Patent [19]

Battilana et al.

[11] 3,947,676

[45] Mar. 30, 1976

[54] PORTABLE HEAD LAMP

[75] Inventors: Remeo A. Battilana; Ann C. Battilana, both of Philadelphia, Pa.

[73] Assignee: The Raymond Lee Organization, Inc., New York, N.Y. ; a part interest

[22] Filed: Nov. 1, 1974

[21] Appl. No.: 519,860

[52] U.S. Cl. .............. 240/6.4 W; 128/23; 240/10.5; 240/59

[51] Int. Cl.$^2$ ...................... F21V 33/00; A61B 1/06

[58] Field of Search .............. 240/6.4 W, 10.5, 10.6, 240/59, 60, 2 ME; 128/23; 350/145, 350/146, 351/16

[56] References Cited

UNITED STATES PATENTS

| | | | |
|---|---|---|---|
| 2,117,967 | 5/1938 | Leipold et al. | 240/59 |
| 2,164,529 | 7/1939 | Koepke | 240/59 |
| 2,176,789 | 10/1939 | Capitani | 240/59 |
| 2,234,995 | 3/1941 | Waechter | 240/59 |
| 2,893,379 | 7/1959 | Springer | 240/59 X |
| 3,087,049 | 4/1963 | Schecter | 240/59 X |
| 3,414,347 | 12/1968 | Stoltze | 350/145 |

*Primary Examiner*—Richard A. Wintercorn
*Attorney, Agent, or Firm*—Daniel Jay Tick

[57] ABSTRACT

An adjustable band is removably mounted on the head of a wearer. A light unit is mounted on the band for illuminating an area in front of the face of the wearer. The light unit comprises a lamp, a battery for energizing the lamp, a switch and a circuit electrically connecting the lamp, battery and switch in a manner whereby the switch selectively controls the energization of the lamp. A magnifying device is movably affixed to the band in a manner whereby in selected positions of the magnifying device, the magnifying device is over the light unit and magnifies and directs illumination produced by the light unit and in other positions of the magnifying device, the magnifying device rests on the head of the wearer.

1 Claim, 4 Drawing Figures

PORTABLE HEAD LAMP

DESCRIPTION OF THE INVENTION

The present invention relates to a portable head lamp.

Objects of the invention are to provide a portable head lamp of simple structure, which is inexpensive in manufacture, is used with facility and convenience, and functions efficiently, effectively and reliably to provide illumination for the user while permitting the hands of the user to be free for desired purposes.

In order that the invention may be readily carried into effect, it will now be described with reference to the accompanying drawing, wherein.

In the FIGS., the same components are identified by the same reference numerals.

The portable head lamp of the invention comprises an adjustable band 1 removably mounted on the head 2 (FIG. 1) of a wearer 3.

Figure 4:
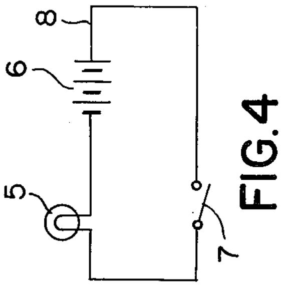
FIG. 4 is a circuit diagram of the light unit of the portable head lamp of the invention.

A light unit 4 is mounted on the band 1 for illuminating an area in front of the face of the wearer 3. The light unit 4 comprises a lamp 5, a battery 6 for energizing the lamp, a switch 7 and a circuit 8 electrically connecting the lamp, battery and switch in a manner whereby the switch selectively controls the energization of the lamp, as shown in FIG. 4.

Figure 1:
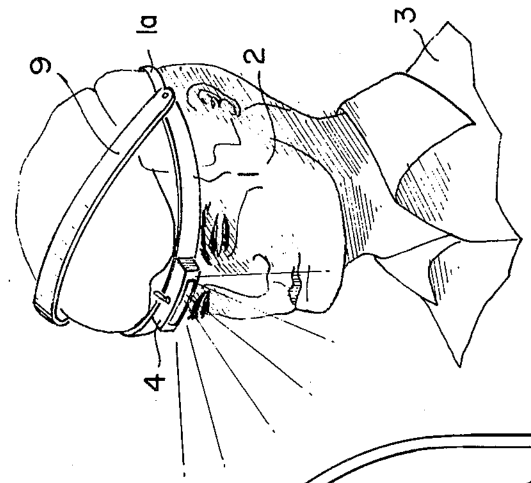
FIG. 1 is a schematic diagram of an embodiment of the portable head lamp of the invention.
Figure 2:
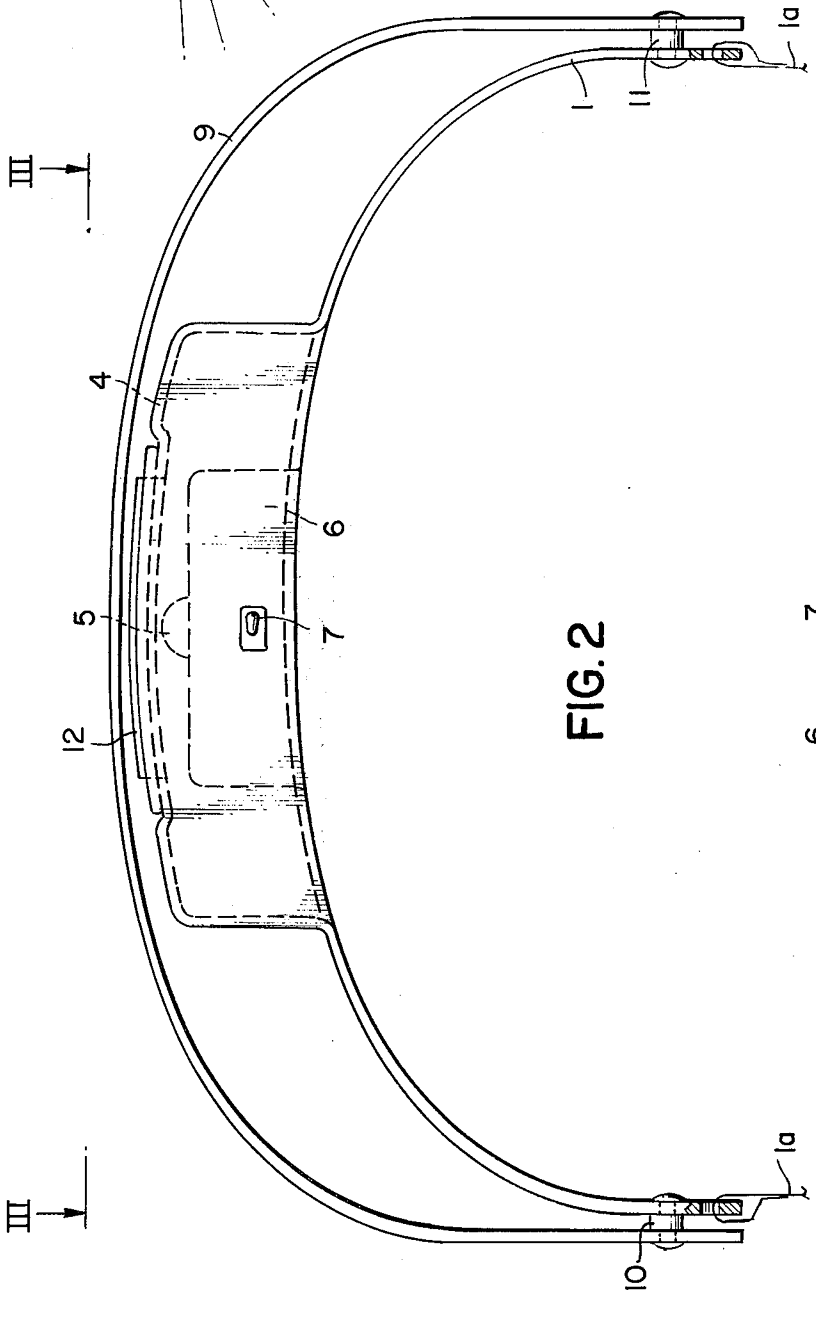
FIG. 2 is a side view, on an enlarged scale, of an embodiment of the portable head lamp of the invention.
Figure 3:
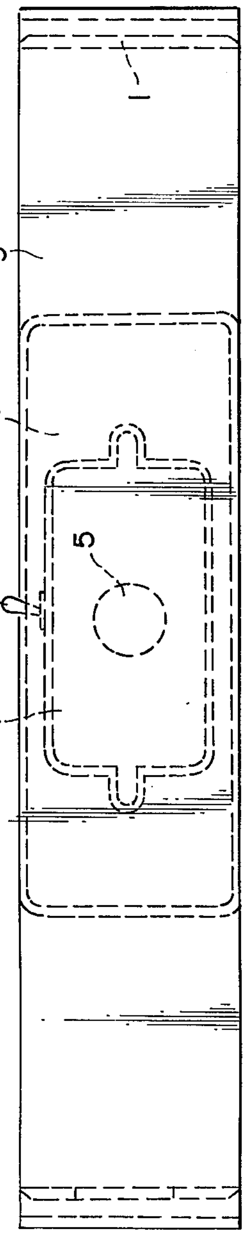
FIG. 3 is a view, taken along the lines III—III, of FIG. 2.

A magnifying device 9 is movably affixed to the band 1 by any suitable means such as, for example, a pair of pivot pins 10 and 11 (FIG. 2), in a manner whereby in selected positions of the magnifying device said magnifying device is over the light unit 4, as shown in FIGS. 2 and 3 and magnifies and directs illumination produced by said light unit. The magnifying device 9 is 1½ to 2 inches wide. In other positions of the magnifying device 9, said magnifying device rests on the head of the wearer, as shown in FIG. 1.

An additional adjustable band, strap or elastic band 1a holds the band 1 on the head of the wearer.

A 3/16 inch magnifying glass or plastic prism 12 is provided in front of the light unit 4.

While the invention has been described by means of a specific example and in a specific embodiment, we do not wish to be limited thereto, for obvious modifications will occur to those skilled in the art without departing from the spirit and scope of the invention.

We claim:

1. A portable head lamp, comprising an adjustable first band removably mounted on the head of a wearer;

a light unit mounted on the first band for illuminating an area in front of the face of the wearer, said light unit comprising a lamp, a battery for energizing the lamp, a switch and a circuit electrically connecting the lamp, battery and switch in a manner whereby the switch selectively controls the energization of the lamp;

a substantially rigid second band pivotally affixed to the first band; and magnifying means affixed to the second band in a manner whereby in selected positions of the second band said magnifying means is over the light unit and magnifies and directs illumination produced by the light unit, and in other positions of the second band said second band rests on the head of the wearer and said magnifying means is spaced from the light unit.

* * * * *